US00PP31544P2

(12) United States Plant Patent
van Sambeek

(10) Patent No.: US PP31,544 P2
(45) Date of Patent: Mar. 10, 2020

(54) ***GAURA* PLANT NAMED 'DOGAURGRALIGHTPINK'**

(50) Latin Name: *Gaura lindheimeri*
Varietal Denomination: Dogaurgralightpink

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/350,467

(22) Filed: Nov. 19, 2018

(51) Int. Cl.
*A01H 5/02* (2018.01)
*A01H 6/00* (2018.01)

(52) U.S. Cl.
USPC ..... Plt./432

(58) Field of Classification Search
USPC ..... Plt./263.1, 432
See application file for complete search history.

(56) References Cited

PUBLICATIONS

Dummen Orange Perennials 2017-2018. https://doc.csod.com/content/doc/publications/11020/index_lms_html5.html. 4 pages. (Year: 2017).*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Gaura* plant named 'Dogaurgralightpink', characterized by its compact, upright to broadly spreading plant habit; vigorous growth habit; freely branching habit; freely flowering habit; light red-colored flowers; and good garden performance.

1 Drawing Sheet

Botanical designation: *Gaura lindheimeri.*
Cultivar denomination: 'DOGAURGRALIGHTPINK'.

BACKGROUND OF THE INVENTION

The present invention relates to a new and distinct cultivar of *Gaura* plant, botanically known as *Gaura lindheimeri* and hereinafter referred to by the name 'Dogaurgralightpink'.

The new *Gaura* is a product of a planned breeding program conducted by the Inventor in Aalsmeer, The Netherlands. The objective of the breeding program is to create new compact and early-flowering *Gaura* plants with attractive leaf and flower coloration.

The new *Gaura* plant originated from a cross-pollination in June, 2014 in Aalsmeer, The Netherlands of a proprietary selection of *Gaura lindheimeri* identified as code number GR-0014, not patented, as the female, or seed, parent with a proprietary selection of *Gaura lindheimeri* identified as code number GR-0007, not patented, as the male, or pollen, parent. The new *Gaura* plant was discovered and selected by the Inventor as a single flowering plant from within the progeny of the stated cross-pollination in a controlled environment in Aalsmeer, The Netherlands in June, 2015.

Asexual reproduction of the new *Gaura* plant by vegetative tip cuttings in a controlled environment in Aalsmeer, The Netherlands since July, 2015 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dogaurgralightpink'. These characteristics in combination distinguish 'Dogaurgralightpink' as a new and distinct *Gaura* plant:

1. Compact, upright to broadly spreading plant habit.
2. Vigorous growth habit.
3. Freely branching habit.
4. Freely flowering habit.
5. Light red-colored flowers.
6. Good garden performance.

Plants of the new *Gaura* can be compared to plants of the female parent selection. Plants of the new *Gaura* differ from plants of the female parent selection in the following characteristics:

1. Plants of the new *Gaura* are more freely branching than plants of the female parent selection.
2. Flower buds of plants of the new *Gaura* are darker in color than flower buds of plants of the female parent selection.

Plants of the new *Gaura* can be compared to plants of the male parent selection. Plants of the new *Gaura* differ from plants of the male parent selection in the following characteristics:

1. Plants of the new *Gaura* are more compact than plants of the male parent selection.
2. Flowers of plants of the new *Gaura* are light red in color whereas flowers of plants of the male parent selection are white in color.

Plants of the new *Gaura* can also be compared to plants of *Gaura lindheimeri* 'Florgaure', disclosed in U.S. Plant Pat. No. 26,518. In side-by-side comparisons, plants of the new *Gaura* differ from plants of 'Florgaure' in the following characteristics:

1. Plants of the new *Gaura* are more freely branching than plants of 'Florgaure'.
2. Flowers of plants of the new *Gaura* are light red in color whereas flowers of plants of 'Florgaure' are red purple in color.

BRIEF DESCRIPTION OF THE PHOTOGRAPH

The accompanying colored photograph illustrates the overall appearance of the new *Gaura* plant showing the colors as true as it is reasonably possible to obtain in colored reproductions of this type. Colors in the photograph may differ slightly from the color values cited in the detailed botanical description which accurately describe the colors of the new *Gaura* plant.

The photograph is a side perspective view of a typical plant of 'Dogaurgralightpink' grown in a container.

DETAILED BOTANICAL DESCRIPTION

The aforementioned photographs and following observations, measurements and values describe plants grown during the summer in 13-cm containers in an outdoor nursery in Aalsmeer, The Netherlands and under cultural practices typical of commercial *Gaura* production. During the production of the plants, day temperatures averaged 20° C. and night temperatures averaged 16° C. Plants were pinched one time one week after planting and were three months old when the photograph was taken and four months old when the description was taken. In the following description, color references are made to The Royal Horticultural Society Colour Chart, 2007 Edition, except where general terms of ordinary dictionary significance are used.

Botanical classification: *Gaura lindheimeri* 'Dogaurgralightpink'.

Parentage:

*Female, or seed, parent*.—Proprietary selection of *Gaura lindheimeri* identified as code number GR-0014, not patented.

*Male or pollen parent*.—Proprietary selection of *Gaura lindheimeri* identified as code number GR-0007, not patented.

Propagation:

*Type*.—By vegetative tip cuttings.

*Time to initiate roots, summer*.—About ten days at temperatures about 26° C.

*Time to initiate roots, winter*.—About two weeks at temperatures about 23° C.

*Time to produce a rooted young plant, summer*.—About twelve days at temperatures about 23° C.

*Time to produce a rooted young plant, winter*.—About 16 days at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous perennial; compact, upright to broadly spreading plant habit; broad inverted triangle in overall shape; freely basal branching habit with about six primary branches with numerous secondary branches developing per plant, pinching enhances lateral branch development; dense and bushy plant form; vigorous growth habit and rapid growth rate.

*Plant height*.—About 20 cm to 25 cm.

*Plant diameter*.—About 27 cm.

Lateral branch description:

*Length*.—About 17 cm.

*Diameter*.—About 1 mm.

*Internode length*.—About 2 cm.

*Strength*.—Strong; flexible.

*Aspect*.—Upright to outwardly.

*Texture and luster*.—Slightly pubescent; slightly glossy.

*Color*.—Close to 146C and 184B.

Leaf description:

*Arrangement*.—Alternate, simple; sessile.

*Length*.—About 6 cm.

*Width*.—About 9 mm.

*Shape*.—Lanceolate.

*Apex*.—Acuminate.

*Base*.—Attenuate.

*Margin*.—Entire; ciliate.

*Texture and luster, upper and lower surfaces*.—Pubescent; slightly glossy.

*Venation pattern*.—Pinnate.

*Color*.—Developing and fully developed leaves, upper surface: Close to 137A; venation, close to 59A. Developing and fully developed leaves, lower surface: Close to 137C; venation, close to 138A.

Flower description:

*Flower arrangement and habit*.—Single flowers arranged on terminal and axillary racemes; freely flowering habit with about 18 flowers per inflorescence and about 1,000 flowers developing during the flowering season; flowers face mostly outwardly to slightly upright.

*Fragrance*.—None detected.

*Natural flowering season*.—Plants flower continuously from May to August in The Netherlands; plants begin flowering about six weeks after planting.

*Flower longevity*.—Individual flowers last about one week on the plant; flowers not persistent.

*Inflorescence height*.—About 7 cm.

*Inflorescence diameter*.—About 4.5 cm.

*Flower diameter*.—About 2.5 cm.

*Flower depth (height)*.—About 1.8 cm.

*Flower buds*.—Length: About 1.5 cm. Diameter: About 2 mm. Shape: Elongated oblong. Color: Close to 53C.

*Petals*.—Arrangement: Four in a single whorl. Length: About 1.8 cm. Width: About 8 mm. Shape: Obovate. Apex: Rounded. Base: Attenuate. Margin: Entire. Texture and luster, upper and lower surfaces: Smooth, glabrous; matte. Color: When opening, upper and lower surfaces: Close to 56D. Fully opened, upper and lower surfaces: Close to 56D; venation, close to 65B; color becoming closer to 65C with development.

*Sepals*.—Arrangement: Four in a single whorl. Length: About 1.8 cm. Width: About 1 mm. Shape: Lanceolate. Apex: Acuminate. Base: Truncate. Margin: Entire. Texture, upper surface: Smooth, glabrous.

Texture, lower surface: Pubescent. Color, upper surface: Close to 59B. Color, lower surface: Close to 63A.

*Peduncles*.—Length: About 13 cm. Diameter: About 1 mm. Strength: Strong. Aspect: Mostly upright. Texture: Pubescent. Color: Close to 148A tinged with close to 187A.

*Pedicels*.—Length: About 2 mm. Diameter: About 0.5 mm. Strength: Moderately strong. Aspect: About 20° from peduncle axis. Texture: Pubescent. Color: Close to 60A.

*Reproductive organs*.—Stamens: Quantity: Eight per flower. Filament length: About 1.4 cm. Filament color: Close to 155D. Anther shape: Linear. Anther length: About 3 mm. Anther color: Close to 187A. Pollen amount: Moderate. Pollen color: Close to 4C. Pistils: Quantity: One per flower. Pistil length: About 1.8 cm. Style length: About 1.7 cm. Style color: Distally, close to 63B; proximally, close to 62D. Stigma shape: Four-parted. Stigma color: Close to 39D. Ovary color: Close to 59A. Seeds and fruits: To date, seed and fruit development have not been observed on plants of the new *Gaura*.

Garden performance: Plants of the new *Gaura* have been observed to have good garden performance and tolerate wind, rain and temperatures ranging from about −20° C. to about 30° C.

Pathogen & pest resistance: To date, plants of the new *Gaura* have not been observed to be resistant to pathogens and pests common to *Gaura* plants.

It is claimed:

1. A new and distinct *Gaura* plant named 'Dogaurgralightpink' as illustrated and described.

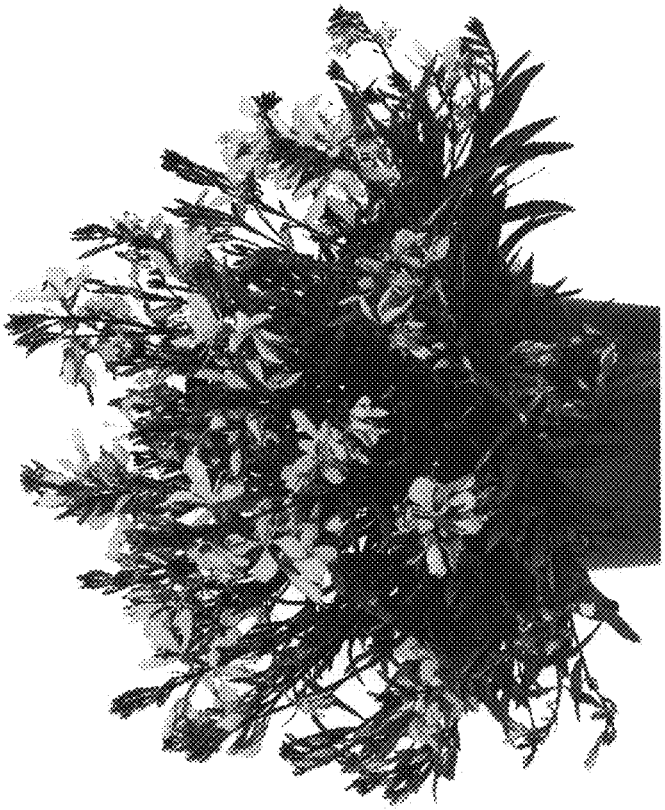

* * * * *